United States Patent
Yang

(10) Patent No.: US 6,669,667 B1
(45) Date of Patent: Dec. 30, 2003

(54) SAFETY SYRINGE

(76) Inventor: Jih-Hsiung Yang, No. 822, Chungcheng Rd., Wufeng Hsiang, Taichung Hsien (TW)

( * ) Notice: Subject to any disclaimer, the term of this patent is extended or adjusted under 35 U.S.C. 154(b) by 0 days.

(21) Appl. No.: 10/411,241

(22) Filed: Apr. 11, 2003

(51) Int. Cl.[7] ................................................. A61M 5/00
(52) U.S. Cl. ........................ 604/110; 604/195; 604/240
(58) Field of Search ................................ 604/158, 218, 604/220, 128, 131, 181, 182, 194, 195, 240, 241–243, 196

(56) References Cited

U.S. PATENT DOCUMENTS 5,007,903 A * 4/1991 Ellard ......................... 604/195

* cited by examiner

Primary Examiner—Manuel Mendez
Assistant Examiner—Kevin C. Sirmons
(74) Attorney, Agent, or Firm—Troxell Law Office PLLC

(57) ABSTRACT

A safety syringe has a hollow barrel, a cord, a needle hub and a plunger. The hollow barrel has a distal open end, a proximal open end, a distal annular rib defined on the inside surface of the proximal open end, a central annular rib defined on the inside surface of the hollow barrel. The needle hub is detachably engaged inside the proximal open end of the hollow barrel and has a needle mounted on the needle hub. The plunger has a push rod and a seal mounted on the push rod, and the seal is slidably mounted inside the hollow barrel. The cord is connected to the needle hub and the seal. When the safety syringe is used, the plunger pulls the cord connected to the needle hub, so the needle hub with the needle is pulled inside the hollow barrel to keep people from being hurt or infected by an exposed.

3 Claims, 5 Drawing Sheets

SAFETY SYRINGE

BACKGROUND OF THE INVENTION

1. Field of the Invention

The present invention relates to a syringe, and more particularly to a safety syringe that can safely hold a used needle and prevent the syringe from being used more than once.

2. Description of Related Art

A conventional syringe has a hollow barrel, a plunger and a needle hub. The needle hubs of conventional syringes are easily inclined during use so the needle hubs are difficult to retract into the barrel. Due to contagious diseases, the needles of syringes and even the hollow barrels and plungers, should not be used again and should be discarded immediately after use. Also, to keep nurses, doctors or workers who deal with discarded syringes from getting injured or infected by used needles, a safety syringe is needed. The conventional safety syringe often has a complex structure, so to provide a simple and effective safe design for the needles of syringes is still needed.

To overcome the shortcomings with conventional syringes, the present invention provides a safety syringe to mitigate or obviate the aforementioned problem.

SUMMARY OF THE INVENTION

The primary objective of the present invention is to provide a safety syringe that has a simpler structure than the conventional safety syringe and improves safety. The safety syringe in accordance with the present invention comprises a hollow barrel, a cord, a needle hub, a plunger and a plunger lock.

The hollow barrel has a distal open end, a proximal open end, a distal annular rib and a central annular rib. The needle hub is detachably mounted inside the proximal open end of the hollow barrel. The plunger has a push rod and a seal mounted on the push rod and is slidably mounted inside the hollow barrel. The cord connects to the needle hub and the seal.

When using the safety syringe, the plunger can pull the cord connected to the needle hub, so the needle hub can be pulled inside the hollow barrel to keep the used needle from injuring or infecting a person.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
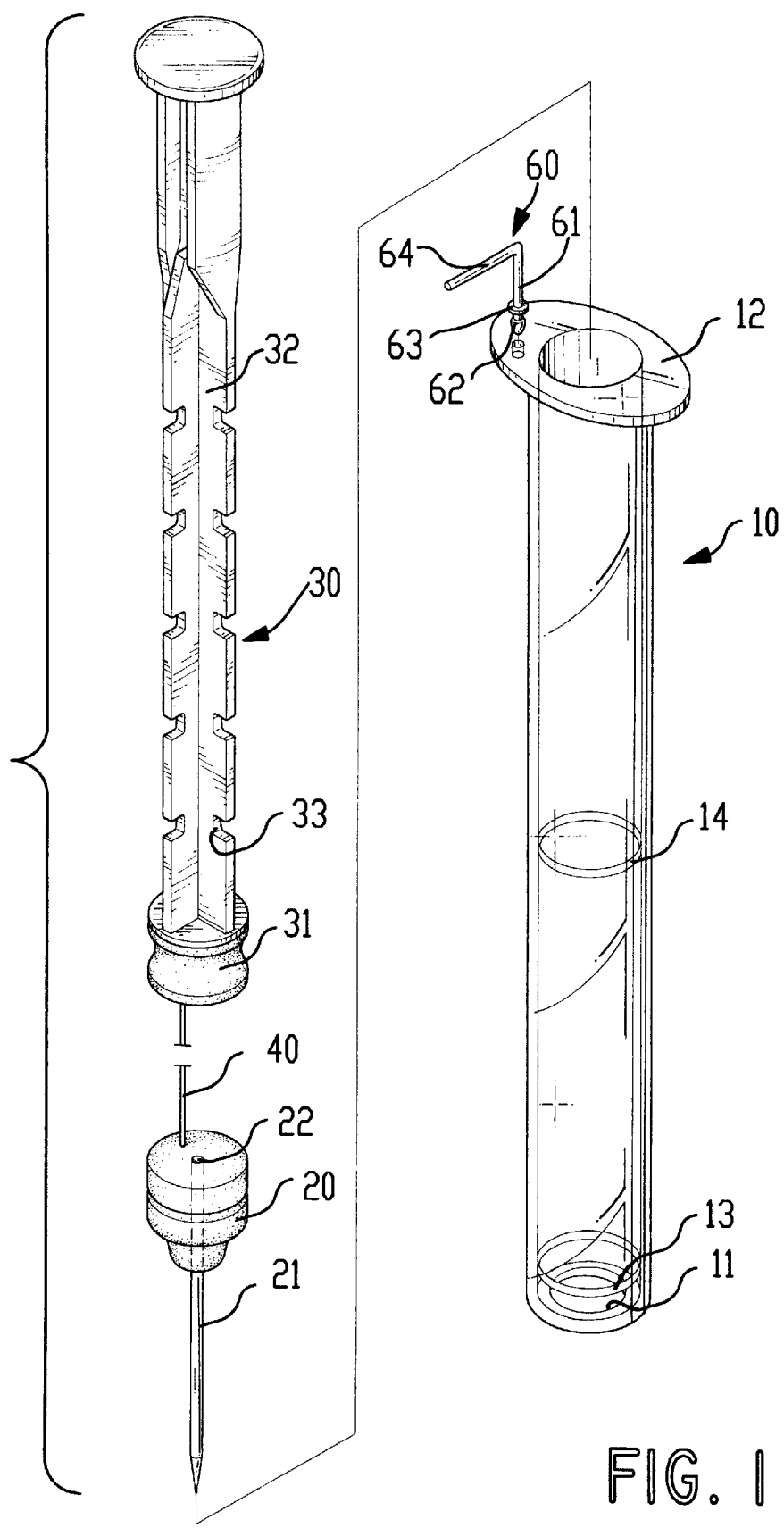
FIG. 1 is an exploded perspective view of the safety syringe in accordance with the present invention.
Figure 2:
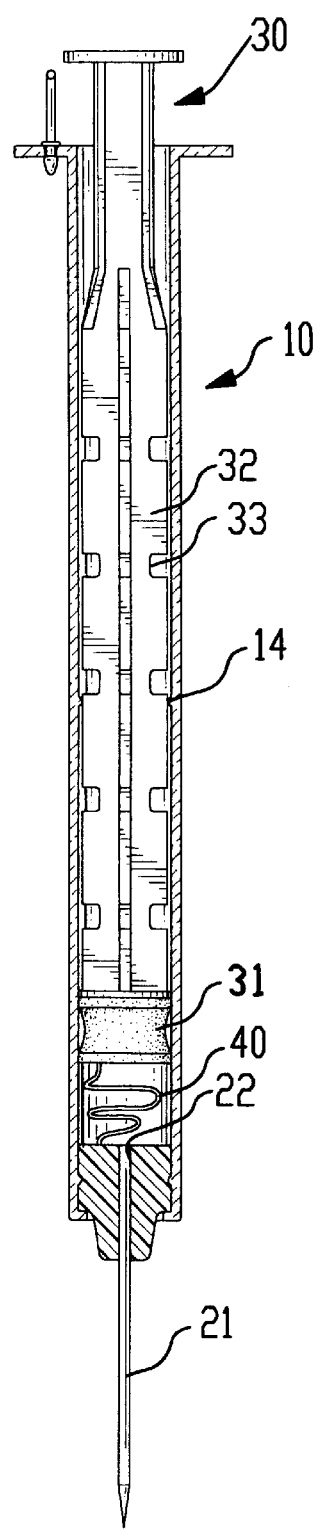
FIG. 2 is a side plan view in partial section of the safety syringe in FIG. 1 with the plunger pressed into the hollow barrel.

With reference to FIGS. 1 and 2, a safety syringe in accordance with the present invention has a hollow barrel (10), a needle hub (20), a plunger (30), a cord (40) and a plunger lock (60).

The hollow barrel (10) is cylindrical and has distal open end (not numbered), a proximal open end (11), an inside surface (not numbered), an outside surface (not numbered), an annular flange (12), a lip (not numbered), a distal annular rib (13) and a central annular rib (14). The annular flange (12) is defined radially around and extends out from the distal open end of the hollow barrel (10). The lip (not numbered) is defined radially around and extends inward from the proximal open end (11) of the hollow barrel (10) so the proximal open end (11) is smaller than the distal open end. The distal annular rib (13) is defined on the inside surface of the hollow barrel (10) near the lip. The central annular rib (14) is defined on the inside surface of the hollow barrel (10) midway between the proximal open end (11) and the distal open end of the hollow barrel (10).

The needle hub (20) is mounted detachably inside the proximal open end (11) of the hollow barrel (10) and has an inside surface (not numbered), an outside surface (not numbered), a needle (21) and a longitudinal passage (22). The needle hub (20) is made of a resilient material. One end of the needle (21) is inserted into the longitudinal passage (22) from the outside surface of the needle hub (20), and the needle (21) has a fluid passage (not numbered) defined through the needle (21). The fluid passage communicates with the inner space of the hollow barrel (10).

The plunger (30) has a distal end (not numbered), a proximal end (not numbered), a seal (31) and a push rod (32). The push rod (32) has a distal end (not numbered), a proximal end (not numbered) and radial protrusions (not numbered). The seal (31) has an inside surface (not numbered) and an outside surface (not numbered). The distal end of the push rod (32) is attached to the outside surface of the seal (31), and the seal (31) is slidably mounted in the hollow barrel (10). The push rod (32) has multiple locking grooves (33) defined radially in the radial protrusions.

The cord (40) has a seal end (not numbered) and a hub end (not numbered). The seal end of the cord (40) is attached to inside surface of the seal (31), and the hub end of the cord (40) is attached to the inside surface of the needle hub (20). The length of the cord (40) is equal to a distance between the inside surface of the needle hub (20) and the inside surface of the seal (31) when the need hub. (20) is engaged with the distal annular rib (13) and the seal abuts the central annular rib (14). Furthermore, a distance between the proximal open end (11) of the hollow barrel (10) and the central annular rib (14) is greater than a combined length of the needle hub (20) and the needle (21) so the needle (21) will be inside the hollow barrel (10) when the needle hub (20) engages the central annular rib (14).

The plunger lock (60) is L-shaped and has a longitudinal leg (61) and a transverse leg (64). The longitudinal leg (61) has a free end, a ball-prong (62) and a limit-ring (63). The ball-prong (62) is formed around the free end of the longitudinal leg (61). The limit-ring (63) is formed around the longitudinal leg (61) of the plunger lock (60) near the ball-prong (62). The ball-prong (62) of the plunger lock (60) is rotatably mounted in the annular flange (12).

Figure 3:
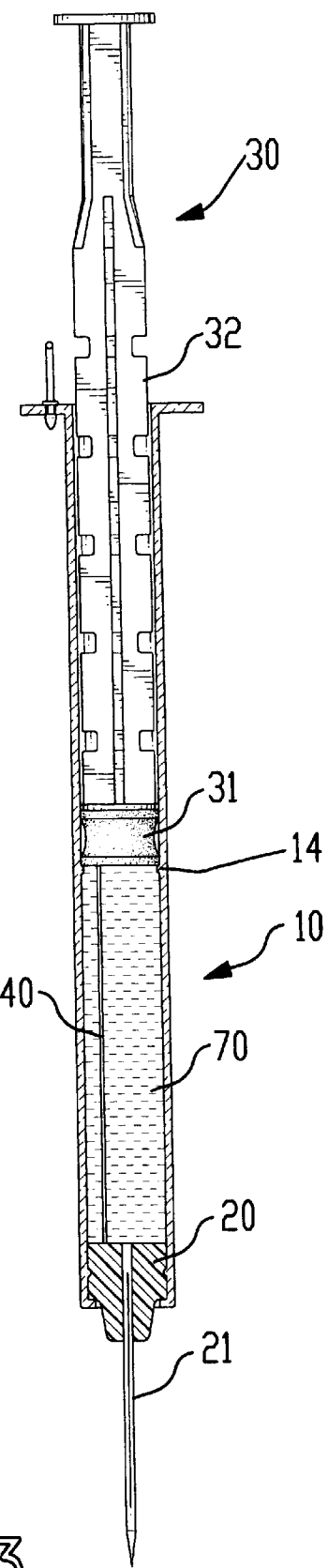
FIG. 3 is an operational side plan view in partial section of the safety syringe in FIG. 1 with a blood sample in the hollow barrel.

With reference to FIGS. 2 and 3, the plunger (30) is pulled toward the distal open end of the hollow barrel (10) after the needle (21) is inserted into a patient's vein to take a blood sample (70). As the seal (31) and the cord (40) are pulled, the blood sample (70) is drawn into the hollow barrel (10) between the seal (31) and the needle hub (20). When the seal (31) moves past the central annular ring (14), drawing the blood sample (70) is finished.

Figure 4:
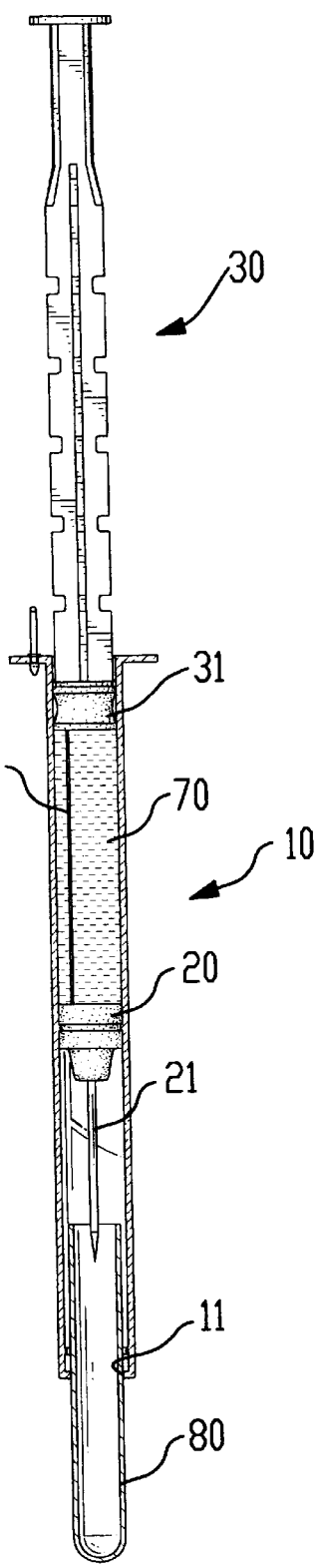
FIG. 4 is an operational side plan view in partial section of the safety syringe in FIG. 1 with a test tube in the hollow barrel to collect the blood sample.
Figure 5:
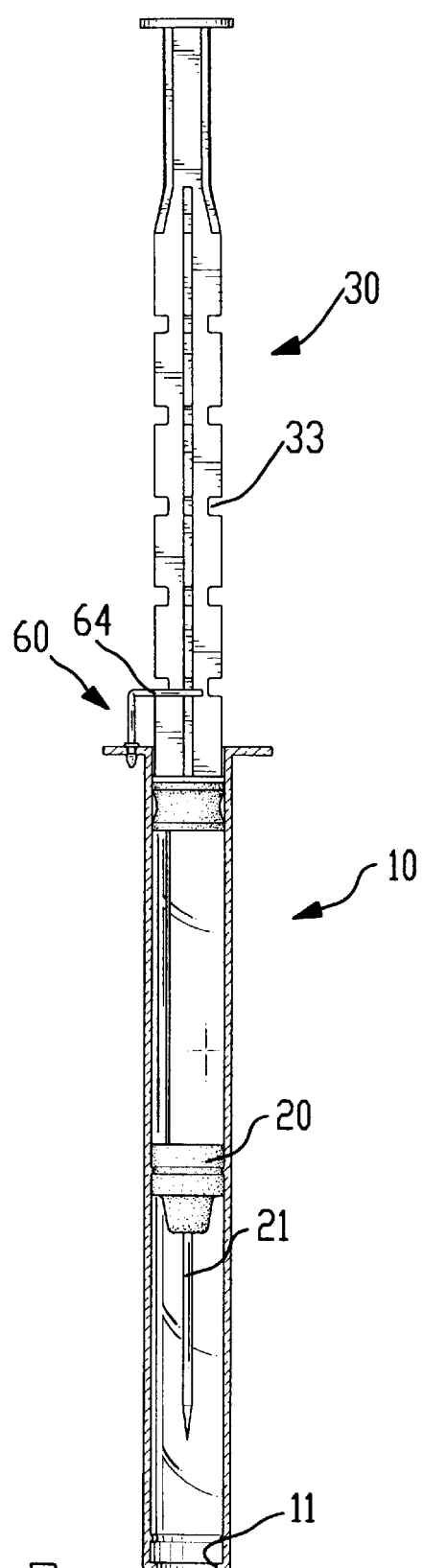
FIG. 5 is an operational side plan view of the safety syringe in FIG. 1 with the push rod locked in position.

With reference to FIGS. 4 and 5, the needle (21) is removed from the patient's vein, and the plunger (30) is pulled toward the distal open end of the hollow barrel (10). The moving plunger (30) pulls the cord (40) and disengages the needle hub (20) from the distal annular rib (13). The plunger (30) continues to pull the needle hub (20) and the blood sample (70) trapped between the seal (31) and the needle hub (20) until the needle hub (20) engages the central annular rib (14). A test tube (80) with an open end (not numbered) is used to collect the blood sample (70). When the needle (21) of the needle hub (20) is totally inside the hollow barrel (10), the open end of the test tube (80) is inserted into the hollow barrel (10) through the proximal open end (11) to collect the blood sample (70). The blood sample (70) is injected into the test tube (80) by pressing the plunger (30). After the blood sample (70) has been injected into the test tube (80), the transverse leg (64) of the plunger lock (60) is pivoted into a corresponding locking groove (33) to ensure that the needle (21) is neither pulled nor pushed out of the hollow barrel (10). Then the test tube (80) is removed from the hollow barrel (10) and capped. The safety syringe can protect people from getting stabbed or infected by the used needle (21) and prevent secondary use of the safety syringe.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising a hollow barrel, a needle hub, a plunger and a cord;
    the hollow barrel being cylindrical and having
        a distal open end;
        a proximal open end;
        an inside surface;
        an outside surface;
        an inner space;
        an annular flange defined radially around and extending out from the distal open end;
        a lip defined radially around and extending inward from the proximal open end of the hollow barrel;
        a distal annular rib defined on the inside surface of the hollow barrel near the lip; and
        a central annular rib defined inside the hollow barrel equidistance between the open proximal end and the open distal end;
    the needle hub detachable engaged to the distal annular rib inside the proximal open end of the hollow barrel and having
        an inside surface;
        an outside surface;
        a needle attached to the outside surface of the needle hub and having a fluid passage communicating with the inner space of the hollow barrel;
        a longitudinal passage defined through the needle hub from the outside surface to the inside surface to receive with one end of the needle;
    the plunger mounted inside the hollow barrel having
        a push rod having
            a proximal end; and
        a seal having
            an outside surface attached to the proximal end of the push rod; and
            an inside surface; and
    the cord having
        a seal end attached to the inside surface of the seal; and
        a hub end attached to the inside surface of the needle hub,
    wherein a distance between the proximal open end of the hollow barrel and the central annular rib is greater than a combined length of the needle hub and the needle.

2. The safety syringe as claimed in claim 1, wherein the cord has a length being equal to a distance between the inside surface of the needle hub and the inside surface of the seal when the needle hub is engaged to the distal annular rib and the inside surface of the seal abuts the central annular rib.

3. The safety syringe as claimed in claim 1, wherein the push rod has a radial protrusions and further comprises multiple locking grooves defined radially in the radial protrusions; and
    a plunger lock being L-shaped and having
        a longitudinal leg having
            a free end;
            a ball-prong formed around the free end of the longitudinal leg and rotatably mounted in the annular flange around the distal end of the hollow tube; and
            a limit-ring defined around the longitudinal leg near the ball-prong; and
    a transverse leg selectively mounted in the locking groove in the push rod to hold the plunger in position.

* * * * *